United States Patent [19]
Le-Khac

[11] Patent Number: 4,731,067
[45] Date of Patent: Mar. 15, 1988

[54] EXTENDED SHELF LIFE WATER-ABSORBING COMPOSITION WHICH FACILITATES FIBER FORMATION

[75] Inventor: Bi Le-Khac, West Chester, Pa.

[73] Assignee: ARCO Chemical Company, Newtown Square, Pa.

[21] Appl. No.: 915,455

[22] Filed: Oct. 6, 1986

[51] Int. Cl.$^4$ ............................................. A61F 13/16
[52] U.S. Cl. ..................................................... 604/367
[58] Field of Search .............. 604/358, 365, 366, 367, 604/372, 374, 375, 376, 377

[56] References Cited

U.S. PATENT DOCUMENTS

| | | |
|---|---|---|
| 4,405,324 | 9/1983 | Cruz, Jr. .............................. 604/376 |
| 4,454,055 | 6/1984 | Richman et al. ..................... 604/376 |
| 4,634,438 | 1/1987 | Sustmann et al. ................... 604/376 |

Primary Examiner—John D. Yasko
Attorney, Agent, or Firm—Dennis M. Kozak

[57] ABSTRACT

A copolymer of recurring units of at least one $\alpha, \beta$-unsaturated monomer and recurring units of at least one copolymerizable comonomer comprising, in its preferred embodiment from about 20 to about 80 percent pendant carboxylic acid units and from about 80 to about 20 percent pendant carboxylate salt units, is blended with at least one monomer containing at least two hydroxyl groups to produce a water-absorbing composition upon curing. The composition is particularly suitable for fiber formation.

17 Claims, No Drawings

EXTENDED SHELF LIFE WATER-ABSORBING COMPOSITION WHICH FACILITATES FIBER FORMATION

This invention relates to water-absorbing compositions.

In one of its more specific aspects, this invention relates to the incorporation of water-absorbing compositions into articles of manufacture for the purpose of improving the absorbent properties of the articles.

Absorbent compositions are widely used in the manufacture of products which require high absorption capability. For example, water-absorbing compositions are used in the manufacture of surgical and dental sponges, tampons, sanitary napkins and pads, bandages, disposable diapers, meat trays, and household pet litter. Water-absorbing compositions are also used for the modification of soil to improve water retention and increase air capacity and for a host of other applications.

As used herein, the term "water" when used in the phrases "water-absorbing" and "water-absorbent" is understood to mean not only water but also electrolyte solutions such as body fluids.

A number of absorbent compositions have been developed which exhibit water absorption capacity. For example, U.S. Pat. Nos. 3,954,721 and 3,983,095 disclose preparations for derivatives of copolymers of maleic anhydride with at least one suitable vinyl monomer in fibrous form. The fibrous copolymers are rendered hydrophilic and water-swellable by reaction with ammonia or an alkali metal hydroxide. U.S. Pat. No. 3,810,468 discloses lightly cross-linked olefin-maleic anhydride copolymers prepared as substantially linear copolymers and then reacted with a diol or a diamine to introduce cross-linking. The resultant lightly cross-linked copolymers are treated with ammonia or an aqueous or alcohol solution of an alkali metal hydroxide. U.S. Pat. No. 3,989,586 describes the preparation of sorptive paper products by incorporating cross-linked copolymers of styrene or olefins with maleic anhydride in a paper web which is then treated to convert the copolymer to a water-swellable salt form. U.S. Pat. No. 3,980,663 describes water-swellable absorbent articles made from carboxylic polyelectrolytes via cross-linking with glycerine diglycidyl ether. U.S. Pat. Nos. 4,332,917 and 4,338,417 disclose blends of copolymers of styrene and maleic anhydride with polymers derived from a monomeric ester having vinyl unsaturation e.g., poly(vinyl acetate), cellulose triacetate, cellulose acetobutyrate, poly(ethylacrylate) and poly(methylmethacrylate). U.S. Pat. No. 4,420,588 teaches a water absorbing rubber composition comprising a 1,3-diene rubber and a water-absorbing resin dispersed in the rubber.

The desirability of having water-absorbing compositions in fibrous forms is well known. For example, in sanitary products such as disposable diapers and tampons, fibers can be more easily confined within the product. In this respect, the prior art water-absorbing compositions are deficient; they do not facilitate fiber formation. Because of the speed of their crosslinking reactions, the prior art water-absorbing compositions possess no appreciable shelf life; fiber formation must be completed shortly after the compositions are prepared. This shelf life deficiency in the prior art compositions is discussed in U.S. Pat. No. 3,983,095 which teaches that fiber formation should be completed within several hours and in some cases immediately, depending upon the reactivity of the cross-linking agent used.

The water-absorbing compositions of this invention possess excellent shelf life and have been found suitable for forming into fibers several months after preparation. They facilitate fiber formation over a wide range of time and temperature. They also possess excellent integrity in the hydrogel or water-swollen state, exhibit excellent water and electrolyte solution absorption capacity, and are readily incorporated into conventional water-absorbing products using conventional methods.

According to this invention there is provided a composition which is water-absorbent upon curing comprising (a) a copolymer containing from about 25 to about 75 mole percent of at least one $\alpha,\beta$-unsaturated monomer bearing at least one pendant unit selected from the group consisting of carboxylic acid units and derivatives of carboxylic acid units and from about 75 to about 25 mole percent of at least one copolymerizable comonomer, wherein from about 20 to about 80 percent of the total pendant units introduced through the $\alpha,\beta$-unsaturated monomer are carboxylic acid units or must be converted into carboxylic acid units, and wherein from about 80 to about 20 percent of the total pendant units are carboxylate metal salt units or must be converted into carboxylate salt units; and (b) at least one monomer containing at least two hydroxyl groups selected from the group consisting of: alkylene glycols containing 2–10 carbon atoms and their ethers; cycloalkylene glycols; Bisphenol A; hydroxy alkylene derivatives of Bisphenol A; hydroquinone; phloroglucinol; hydroxy alkylene derivatives of diphenols; glycerol; erythritol; pentaerythritol; and all natural monosaccharides.

According to this invention there is provided a method of producing a water-absorbing composition comprising the steps of: (a) preparing a blend of (i) a copolymer containing from about 25 to about 75 mole percent recurring units of at least one $\alpha,\beta$-unsaturated monomer which bears at least one pendant unit selected from the group consisting of carboxylic acid units and derivatives of carboxylic acid units, and from about 75 to 25 mole percent recurring units of at least one copolymerizable comonomer, wherein from about 20 to about 80 mole percent of the total pendant units introduced through the recurring $\alpha,\beta$-unsaturated monomer units are carboxylic acid units or must be converted into carboxylic acid units and wherein from about 80 to about 20 percent of the total pendant units are carboxylate salt units or must be converted into carboxylate salt units; and (ii) at least one monomer containing at least two hydroxyl groups selected from the group consisting of: alkylene glycols containing 2–10 carbon atoms and their ethers; cycloalkylene glycols; Bisphenol A; hydroxy alkylene derivatives of Bisphenol A; hydroquinone; phloroglucinol; hydroxy alkylene derivatives of diphenols; glycerol; erythritol; pentaerythritol; and all natural monosaccharides; and (b) curing the resulting blend.

According to this invention there is provided a method of absorbing water and electrolyte solutions comprising the step of contacting the water or electrolyte solution to be absorbed with a cured water absorbing composition comprising a blend of: (a) a copolymer containing from about 25 to about 75 mole percent of at least one $\alpha,\beta$-unsaturated monomer bearing at least one pendant unit selected from the group consisting of carboxylic acid units and derivatives of carboxylic acid units and from about 75 to 25 mole percent of at least one copolymerizable comonomer, wherein from about 20 to about 80 percent of the total pendant units introduced through the α,β-unsaturated monomer are carboxylic acid units or must be converted into carboxylic acid units, and wherein from about 80 to about 20 percent of the total pendant units are carboxylate salt units or must be converted into carboxylate salt units; and (b) at least one monomer containing at least two hydroxyl groups selected from the group consisting of: alkylene glycols containing 2-10 carbon atoms and their ethers; cycloalkylene glycols; Bisphenol A; hydroxy alkylene derivatives of Bisphenol A; hydroquinone; phloroglucinol; hydroxy alkylene derivatives of diphenols; glycerol; erythritol; pentaerythritol; and all natural monosaccharides.

An article of manufacture comprising a cured water-absorbing composition and a means for supporting said composition to present said composition for absorption usage, wherein said water-absorbing composition comprises a blend of: (a) a copolymer containing from about 25 to about 75 mole percent of at least one α,β-unsaturated monomer bearing at least one pendant unit selected from the group consisting of carboxylic acid units and derivatives of carboxylic acid units and from about 75 to about 25 mole percent of at least one copolymerizable comonomer, wherein from about 20 to 80 percent of the total pendant units introduced through the α, β-unsaturated monomer are carboxylic acid units or must be converted into carboxylic acid units, and wherein from about 80 to about 20 percent of the total pendant units are carboxylate salt units or must be converted into carboxylate salt units; and (b) at least one monomer containing at least two hydroxyl groups selected from the group consisting of: alkylene glycols containing 2-10 carbon atoms and their ethers; cycloalkylene glycols; Bisphenol A; hydroxy alkylene derivatives of Bisphenol A; hydroquinone; phloroglucinol; hydroxy alkylene derivatives of diphenols; glycerol; erythritol; pentaerythritol; and all natural monosaccharides.

According to this invention there is also provided a method of enhancing at least one water absorbing characteristic of an article which method comprises the step of incorporating into the article a cured water-absorbing composition comprising a blend of: (a) a copolymer containing from about 25 to about 75 mole percent of at least one α,β-unsaturated monomer bearing at least one pendant unit selected from the group consisting of carboxylic acid units and derivatives of carboxylic acid units and from about 75 to about 25 mole percent of at least one copolymerizable comonomer, wherein from about 20 to about 80 percent of the total pendant units introduced through the α,β-unsaturated monomer are carboxylic acid units or must be converted into carboxylic acid units, and wherein from about 80 to about 20 percent of the total pendant units are carboxylate salt units or must be converted into carboxylate metal salt units; and (b) at least one monomer containing at least two hydroxyl groups selected from the group consisting of: alkylene glycols containing 2-10 carbon atoms and their ethers; cycloalkylene glycols; Bisphenol A; hydroxy alkylene derivatives of Bisphenol A; hydroquinone; phloroglucinol; hydroxy alkylene derivatives of diphenols; glycerol; erythritol; pentaerythritol; and all natural monosaccharides, said composition being incorporated into the article in an effective amount to enhance at least one waterabsorbing characteristic of the article as compared to the water-absorbing characteristics of the article in the absence of the composition.

Copolymers suitable for use to produce water-absorbing compositions of the invention will contain from about 25 to about 75 total mole percent recurring units of at least one α,β-unsaturated monomer and from about 75 to about 25 total mole percent recurring units of at least one copolymerizable comonomer. Preferably, the copolymer will contain from about 35 to about 65 total mole percent of recurring units of at least one α,β-unsaturated monomer and from about 65 to about 35 total mole percent of at least one copolymerizable comonomer. Most preferably, the copolymer will be an equimolar copolymer.

Suitable α,β-unsaturated monomers are those bearing at least one pendant carboxylic acid unit or derivative of a carboxylic acid unit. Derivatives of carboxylic acid units include carboxylic acid salt groups, carboxylic acid amide groups, carboxylic acid imide groups, carboxylic acid anhydride groups and carboxylic acid ester groups.

Suitable α,β-unsaturated monomers include maleic acid; crotonic acid; fumaric acid; mesaconic acid; the sodium salt of maleic acid; the sodium salt of 2-methyl, 2-butene dicarboxylic acid; the sodium salt of itaconic acid; maleamic acid; maleamide; N-phenyl maleimide; maleimide; maleic anhydride; fuameric anhydride; itaconic anhydride; citraconic anhydride; mesaconic anhydride; methyl itaconic anhydride; ethyl maleic anhydride; diethylmaleate; methylmaleate; and the like, and their mixtures.

Any suitable copolymerizable comonomer can be employed. Suitable copolymerizable comonomers include ethylene, propylene, isobutylene, $C_1$ to $C_4$ alkyl methacrylates, vinyl acetate, methyl vinyl ether, isobutyl vinyl ether, and styrenic compounds having the formula:

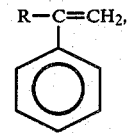

wherein R represents hydrogen or an alkyl group having from 1 to 6 carbon atoms and wherein the benzene ring may be substituted with low molecular weight alkyl or hydroxy groups.

Suitable $C_1$ to $C_4$ alkyl acrylates include methyl acrylate, ethyl acrylate, isopropyl acrylate, n-propyl acrylate, n-butyl acrylate, and the like, and their mixtures.

Suitable $C_1$ to $C_4$ alkyl methacrylates include methyl methacrylate, ethyl methacrylate, isopropyl methacrylate, n-propylmethacrylate, n-butyl methacrylate, and the like, and their mixtures.

And, suitable styrenic compounds include styrene, α-methylstyrene, p-methylstyrene, t-butyl styrene, and the like, and their mixtures.

The pendant units on the α,β-unsaturated monomer, will determine what, if any, additional reactions must be carried out to obtain a copolymer having the requisite pendant units necessary to produce the water-absorbing compositions of this invention about 20 to about 80 percent pendant carboxylic acid units and about 80 to about 20 percent pendant carboxylate salt units. Preferably, both units are present in an amount of from about 30 to about 70 percent.

In general, if the α,β-unsaturated monomer bears only carboxylic acid amide, carboxylic acid imide, carboxylic acid anhydride, carboxylic acid ester groups, or mixtures thereof, it will be necessary to convert at least a portion of such carboxylic acid derivative groups to carboxylic acid groups by, for example, a hydrolysis reaction. If the α,β-unsaturated monomer bears only carboxylic acid salt groups, acidification to form carboxylic acid groups will be necessary.

Similarly, the final copolymer must contain from about 80 to 20 percent pendant carboxylate salt units. Accordingly, it may be necessary to carry out a neutralization reaction. Neutralization of carboxylic acid groups with a strong organic or inorganic base such as NaOH, KOH, ammonia, ammonia-in-water solution, or organic amines will result in the formation of carboxylate salt units, preferably carboxylate metal salt units.

Moreover, the sequence and the number of reactions (hydrolysis, acidification, neutralization, etc.) carried out to obtain the desired functionality attached to copolymer backbone are not critical. Any number and sequence resulting in a final copolymer which possesses from about 20 to about 80 percent pendant carboxylic acid units and from about 80 to about 20 percent pendant carboxylate salt units is suitable.

One copolymer particularly suitable for use is a copolymer of maleic anhydride and isobutylene. Another is maleic anhydride and styrene. Suitable copolymers will have peak molecular weights of from about 5,000 to about 500,000 or more.

Suitable copolymers of maleic anhydride and isobutylene can be prepared using any suitable conventional method. Such copolymers are also commercially available from Kuraray Isoprene Chemical Company, Ltd., Tokyo, Japan, under the trademark ISOBAM. ISOBAM copolymers are available in several grades which are differentiated by viscosity molecular weight: ISOBAM-10, 160,000 to 170,000; ISOBAM-06, 80,000 to 90,000; ISOBAM-04, 55,000 to 65,000; and ISOBAM-600, 6,000 to 10,000.

To produce a water-absorbing composition of this invention, at least one copolymer as described above and at least one monomer bearing at least two hydroxyl groups are blended such that the water-absorbing composition contains in weight percent, from about 80 to about 99.5 total copolymer and from about 0.5 to about 20 total monomer. Preferably, the composition will contain from about 90 to about 99 weight percent total copolymer and from about 1 to about 10 weight percent total monomer.

Any suitable monomer bearing at least two hydroxyl groups and having a relatively low molecular weight, less than 1,000, can be employed in the practice of this invention.

Suitable monomers include ethylene glycol, propylene glycol, trimethylene glycol, 1,4-butane diol, 2-methyl 1,3-propane diol, neopentyl glycol, 1,5-pentane diol, diethylene glycol, dipropylene glycol, 1,4-cyclohexane dimethanol, Bisphenol A, 1,4-bis-(β-hydroxyethoxy)bisphenol, hydroquinone, phloroglucinol, glycerol, erythritol, pentaerythritol, 1,7-dihydroxysedoheptulose, and the like.

Particularly suitable monomers for use in the practice of this invention are ethylene glycol, propylene glycol, 1,4-butane diol, diethylene glycol, and glycerol.

The water-absorbing composition of this invention can be prepared using any suitable blending method such as described in the Examples which follow. After the water-absorbing composition is prepared, but typically before it is cured but in some instances as it is curing, it is processed into any desired form using conventional methods of fabrication. For example, the water-absorbing composition can be subjected to casting; spray drying; air-assisted spray drying; air attenuation; wet, dry or flash spinning; and the like. The selection of the process is typically dictated by the shape or form needed for end use. Forms that the water-absorbing composition may be fabricated into include films or sheets, powders and granules, fibers and any form into which fibers can be processed such as for example milled fibers, chopped fibers, fluff or bulk fibers, strands, yarns, woven fabrics, non-woven mats and the like using a variety of methods, including twisting, beaming, slashing, warping, quilling, severing, texturizing, weaving, knitting, braiding etc.

While not meaning to be limited to any theory, the monomer bearing at least two hydroxyl groups is believed to serve as a high temperature, slow-reacting, cross-linking type agent for the copolymer particles resulting in the formation of covalent cross-link type bonds upon curing. For example, it has been found that, if a partially neutralized styrene-maleic anhydride copolymer is blended with propylene glycol to form a water-absorbing composition according to this invention, a temperature about 150° C. or higher is typically required to achieve cure. Similarly, if a partially neutralized ethylene-maleic anhydride copolymer is employed, a temperature of 140° C. or higher is typically needed to achieve cure. And, if a partially neutralized isobutylene-maleic anhydride copolymer is employed, a temperature of 200° C. or higher is typically needed to achieve cure.

Without meaning to limit the invention, the waterabsorbing compositions of this invention are particularly well suited for being made into fibers because of the wide time and temperature ranges over which they can be shaped. More specifically, the water-absorbing compositions of this invention can be formulated to cure at temperatures within the range of from about 140° C. to about 250° C. or higher and possess shelf lives in excess of two months, as demonstrated in Example 7. Hence, the water-absorbing compositions of this invention can be easily made into fibers using conventional fiber-forming methods and equipment. Moreover, no post-treatment (e.g., a salt-forming reaction as taught in U.S. Pat. No. 3,983,095) of the cured fiber products is required.

The water-absorbing compositions of this invention and articles of manufacture into which the compositions are incorporated are suitable for use in a wide range of absorptive functions. In general, the articles into which the water-absorbing compositions are incorporated serve the function of supporting the composition and presenting it in a form adapted for absorptive end use. Means to support and present the composition for absorptive use include, but are not meant to be limited to bandages, surgical and dental sponges, tampons, sanitary napkins and pads, disposable diapers, meat trays, pads for absorption of perspiration, and the like.

In one embodiment, a water-absorbing composition of this invention is incorporated into a disposable diaper, using conventional fabrication methods to form a diaper composite having the following typical layers: (1) an outer layer (away from the body) of impermeable polyethylene film; (2) a first cellulosic pulp layer superimposed on the film; (3) a layer of (i) a cured waterabsorbing composition of this invention in the form of, for example, fluff, a fibrous mass, a non-woven fiber mat or a woven fabric; or (ii) a layer comprising a blend of a cured water-absorbing composition of this invention and another fluff conventionally employed in diapers; (4) an optional, second cellulosic pulp layer; and (5) an inner permeable polyethylene film layer.

Fibers made from the water-absorbing compositions of this invention are particularly suitable for absorbent applications. It is well known that a mass of fibers provides a large surface area for contact with the liquid material to be absorbed. Fibers as compared to powders can also be more easily confined within the article into which they are incorporated.

The following examples serve to further demonstrate the invention.

EXAMPLE 1

This example demonstrates the preparation of a series of water-absorbing compositions of the invention using ISOBAM 10 isobutylene/maleic anhydride copolymer commercially available from Kuraray Isoprene Chemical Company, Limited. ISOBAM 10 has a molecular weight of 170,000 and a maleic anhydride content of about 59.3 weight percent (46.6 mole %) as determined by titration of maleic acid. Four water-absorbing compositions (I-IV) were separately prepared as follows.

About 1270 g of ISOBAM 10 isobutylene/maleic anhydride copolymer and about 2007 g of demineralized water were added to a mixing vessel with agitation and the vessel contents were heated to about 90° C. At a temperature of about 90° C. about 658 g of a 50% sodium hydroxide solution prepared from 98.9% pure sodium hydroxide pellets were slowly added to the mixing vessel over a one hour period with agitation. After the addition of the sodium hydroxide solution, agitation was continued for about 12 hours at 90° C. to complete the reaction.

The pH of the solution was found to be 6.5 and the neutralization reaction was calculated to have converted about 53.5% of the pendant carboxylic acid units on the 46.6 mole % anhydride units into carboxylate sodium salt units. The balance of the pendant units were converted to carboxylic acid units.

As shown in the following Table 1, four water-absorbing compositions of the invention were separately prepared using the above aqueous solution of partially neutralized isobutylene/maleic anhydride copolymer. Each of the four compositions was prepared by adding a predetermined amount of propylene glycol to a certain amount of copolymer solution and stirring for about 30 minutes. After stirring, each solution was separately heated to drive off excess water and to provide solutions of approximately a 45% solids content suitable for fiber formation using a dry spinning process.

TABLE 1

| Composition | I | II | III | IV |
|---|---|---|---|---|
| Partially neutralized isobutylene/maleic anhydride copolymer solution (g) | 213.25 | 203.57 | 198.83 | 222.52 |
| Propylene glycol |  |  |  |  |
| (g) | 2.06 | 3.29 | 4.49 | 7.18 |
| (phr) based on copolymer | 3 | 5 | 7 | 10 |

Fibers having diameters of from about 5-25 microns were separately produced from Compositions I-IV by dry spinning. A sample of fibers produced from each composition was cured by heating at about 210° C. for 30 minutes and tested for absorbency. Each sample of fibers was tested to determine Swell Index and Percent Solubility using the following test procedures.

Swell Index

This test procedure is described in U.S. Pat. No. 4,454,055 the teachings of which are incorporated herein by reference thereto. The test procedure and equipment used herein were modified slightly as compared to the procedure and equipment described in U.S. Pat. No. 4,454,055.

To determine the Swell Index at atmospheric (room) pressure, about 0.2 to 0.3 g of the water-absorbing composition to be tested is placed in an empty W-shaped tea bag. The tea bag containing the composition is immersed in brine (0.9 wt. % NaCl) for 10 minutes, removed and allowed to sit on a paper towel for 30 seconds to remove surface brine. The Swell Index of the composition, that is, the units of liquid absorbed per each unit of sample is calculated using the following formula:

$$\text{Swell Index} = \frac{\text{Weight of Wet Composition}}{\text{Weight of Dry Composition}} - 1$$

To determine Swell Index under pressure, the following modified procedure was used.

After the tea bag containing the sample composition is immersed in brine and surface brine is removed, it is immediately placed in a 16 cm ID Buchner funnel fitted with a 2000 ml sidearm vacuum filter flask and connected to a manometer. Then, a piece of dental dam rubber sheeting is securely fixed over the mouth of the funnel such that the sheeting just rests on the tea bag. Next, a vacuum sufficient to create the desired pressure is drawn on the flask for a period of five minutes, and, the Swell Index under pressure is calculated using the above formula.

Percent Solubility

About 0.5 g of the water-absorbing composition sample to be tested is dispersed in about 150 g of brine (0.9 wt. % NaCl) at room temperature for 20 minutes with occasional gentle agitation. After 20 minutes, the mixture is filtered through a 150 micron polypropylene screen. Next, the filtrate is dried to a constant weight in an oven and the weight of soluble composition determined by subtracting the weight of the NaCl from the total weight of the dry filtrate. Percent solubility is then determined using the following formula:

$$\text{Percent Solubility} = \frac{\text{Weight of Soluble Composition}}{\text{Weight of Sample Composition}} \times 100$$

The test results for the fiber samples of Compositions I-IV are shown in Table 2.

TABLE 2

| Composition | I | II | III | IV |
| --- | --- | --- | --- | --- |
| Propylene glycol (phr) | 3 | 5 | 7 | 10 |
| Swell Index | | | | |
| Atmospheric Pressure | 46.3 | 39.5 | 28.8 | 27.2 |
| 0.5 psi | 29.1 | 26.2 | 19.9 | 17.8 |
| % Solubility | 23.9 | 17.9 | 11.7 | 7.9 |

EXAMPLE 2

This example demonstrates the preparation of a waterabsorbing composition of this invention using ISOBAM 10 isobutylene/maleic anhydride copolymer and ethylene glycol. Fibers produced from the composition were cured at different temperatures and the effect of curing at the different temperatures is shown in Table 3.

Using substantially the procedure of Example 1, about 226.13 g of the aqueous solution of the partially neutralized isobutylene/maleic anhydride copolymer produced in Example 1 were mixed with about 2.19 g of ethylene glycol and concentrated to give a 45% solids composition (Composition V) containing 3 phr of ethylene glycol based on the weight of the isobutylene/maleic anhydride copolymer. About 20–25 micron diameter fibers were prepared from the composition as described in Example 1. The absorbency of the fibers and the effect of three different cure temperatures, 190° C., 200° C., and 210° C. on samples of the fibers are shown in following Table 3.

TABLE 3

| Composition | V | V | V |
| --- | --- | --- | --- |
| Cure Temperature (°C.) | 190 | 200 | 210 |
| Swell Index | | | |
| Atmospheric Pressure | 39.9 | 37.2 | 32.5 |
| 0.5 psi | 25.5 | 24.5 | 20.1 |
| % Solubility | 15.9 | 11.4 | 7.7 |

EXAMPLE 3

This example demonstrates the preparation of a water-absorbing composition of this invention using ISOBAM 10 isobutylene/maleic anhydride copolymer and 1,4-butane diol. Fibers produced from the composition were cured at different temperatures and the effect of curing at different temperatures is shown in Table 4.

Using substantially the procedure of Example 1, about 150.07 g of the aqueous solution of the partially neutralized isobutylene/maleic anhydride copolymer produced in Example 1 were mixed with about 3.39 g of 1,4-butane diol and concentrated to give a 45% solids composition (Composition VI) containing 7 phr of 1,4-butane diol based on the weight of the isobutylene/maleic anhydride copolymer. About 5–10 micron diameter fibers were prepared from the composition as described in Example 1. The absorbency of the fibers and the effect of three different cure temperatures, 170° C., 180° C., and 190° C., on samples of the fibers are shown in following Table 4.

TABLE 4

| Fibers of Composition | VI | VI | VI |
| --- | --- | --- | --- |
| Cure Temperature (°C.) | 170 | 180 | 190 |
| Swell Index | | | |
| Atmospheric Pressure | 39.4 | 36.4 | 27.5 |
| 0.5 psi | 25.9 | 23.5 | 16.2 |
| % Solubility | 15.1 | 8.0 | 5.4 |

EXAMPLE 4

This example demonstrates the preparation of different diameter fibers from a water-absorbing composition of this invention and shows the effect of fiber diameter on the absorbency of fibers of the same composition (Composition VII). Substantially the same materials and procedures of Example 1 were employed.

About 1270 g of isobutylene/maleic anhydride copolymer and about 2007 g of demineralized water were added to a mixing vessel with stirring and heated to about 90° C. About 658.3 g of a 50% sodium hydroxide solution were added slowly over a one hour period. The reactor contents were stirred for about one hour, and then about 88.96 g (7 phr) of propylene glycol were added to the reactor. The reactor contents were stirred for about 9 hours at 90° C.

A vacuum pump equipped with a cold trap was hooked to the top of the mixing vessel and excess water was removed to yield an aqueous solution having a solids content of about 55%.

The 55% solids solution was charged into a holding tank equipped with two 0.020" nozzles located at the bottom of the tank. The solution was extruded through the nozzles under pressure into fibers which were wound onto a take-off roller. Fibers of different diameters were prepared by changing the speed of the take-off rollers and thus the speed at which fibers were drawn.

Four different diameter fibers were produced and cured at 210° C. for about 30 minutes. The absorbency of the fibers and the effect of fiber diameter on the absorbency of the fibers are shown in Table 5.

TABLE 5

| Fibers of Composition | VII | VII | VII | VII |
| --- | --- | --- | --- | --- |
| Fiber Diameter (microns) | 10 | 25 | 100 | 175 |
| Swell Index | | | | |
| Atmospheric Pressure | 33.0 | 33.8 | 46.5 | 50.8 |
| 0.5 psi | 25.0 | 22.2 | 30.2 | 35.0 |
| % Solubility | 14.1 | 15.2 | 7.2 | 11.9 |

EXAMPLE 5

This example demonstrates the preparation of a water-absorbing composition of this invention using ISOBAM 10 isobutylene/maleic anhydride copolymer and glycerol. Fiber produced from the composition (Composition VIII) were cured at two different temperatures, and the effect of the different cure temperatures is shown in Table 6.

Using substantially the procedure of Example 1, about 2869 g of the aqueous solution of the partially neutralized isobutylene/maleic anhydride copolymer of Example 1 were mixed with 64.8 g of glycerol and concentrated to give a 45% solids composition containing 7 phr glycerol based on the weight of the isobutylene/maleic anhydride copolymer. Samples of fibers having diameters of about 10 microns were produced by dry spinning and separately cured at 170° C. and 180° C.

for 30 minutes and tested for absorbency. The test results are shown in Table 6.

TABLE 6

| Fibers of Composition | VIII | VIII |
|---|---|---|
| Cure Temperature (°C.) | 170 | 180 |
| Swell Index | | |
| Atmospheric Pressure | 43.8 | 34.2 |
| 0.5 psi | 28.3 | 24.9 |
| % Solubility | 16.7 | 11.7 |

EXAMPLE 6

This example demonstrates the preparation of a water-absorbing composition of this invention using ISOBAM 10 isobutylene/maleic anhydride copolymer and diethylene glycol. Fibers produced from the composition (Composition IX) were cured at two different temperatures, and the effect of the different cure temperatures is shown in Table 7.

Using substantially the procedure of Example 1, about 09.22 g of the aqueous solution of the partially neutralized isobutylene/maleic anhydride copolymer of Example 1 were mixed with 2.47 g of diethylene glycol and concentrated to give a 45% solids composition containing 7 phr diethylene glycol based on the weight of the isobutylene/maleic anhydride copolymer. Samples of fibers having diameters of about 10-20 microns were produced by dry spinning and separately cured at 170° C. and 180° C. for 30 minutes and tested for absorbency. The test results are shown in Table 7.

TABLE 7

| Fibers of Composition | IX | IX |
|---|---|---|
| Cure Temperature (°C.) | 170 | 180 |
| Swell Index | | |
| Atmospheric Pressure | 58.8 | 38.3 |
| 0.5 psi | 41.3 | 32.9 |
| % Solubility | 21.6 | 12.7 |

EXAMPLE 7

This example demonstrates that the water-absorbing compositions of this invention possess excellent shelf-life in solution form. A sample of the aqueous solution prepared according to the procedure of Example 5 was aged at 90° C. in a closed container. Solution viscosity measurements using a Brookfield viscometer were taken after 6, 29, 35 and 41 hours aging. The viscosities measured are listed in Table 8, below. After 41 hours no gel formation was observed in the solution.

TABLE 8

| Compostion (aqueous solution) Aging Time at 90° C. | VIII Viscosity (Poises) |
|---|---|
| 0 hr | 700 |
| 6 hrs | 773 |
| 29 hrs | 802 |
| 35 hrs | 757 |
| 41 hrs | 776 |

Another sample of the aqueous solution of Example 5 was aged for 11 weeks at ambient temperature. After 11 weeks aging, fibers were prepared from the aged solution and the resulting fibers were cured at 180° C. for 30 minutes.

The absorbent property data of the resulting fibers prepared after 11 weeks compared with the absorbent property data of the fibers produced from the same composition (Example 5) but in the absence of aging, the composition is shown in Table 9.

TABLE 9

| Fiber of Composition | VIII | VIII |
|---|---|---|
| Time of Solution Aging | 0 | 11 weeks |
| Swell Index: | | |
| Atomospheric Pressure | 34.2 | 41.2 |
| 0.5 psi | 24.9 | 30.3 |

The above data demonstrate that fibers of the invention produced after eleven weeks aging from the composition of Example 5 do not lose their absorbent properties as compared to the absorbent properties of fibers prepared in the absence of aging.

It will be evident from the foregoing that various modifications can be made to this invention. Such, however, are considered as being within the scope of the invention.

What is claimed is:

1. An article of manufacture comprising a cured water-absorbing composition and a means for supporting said composition for absorption usage, wherein said water-absorbing composition comprises a blend of:
   (a) a copolymer containing from about 25 to about 75 mole percent recurring units of at least one $\alpha,\beta$-unsaturated monomer bearing at least one pendant unit selected from the group consisting of carboxylic acid units and derivatives of carboxylic acid units and from about 75 to about 25 mole percent recurring units of at least one copolymerizable comonomer, wherein from about 20 to about 80 percent of the total pendant units introduced through the recurring units of the $\alpha,\beta$-unsaturated monomer must either be carboxylic acid units or must be converted into carboxylic acid units, and wherein from about 80 to about 20 percent of the total pendant units must either be carboxylate salt units or must be converted into carboxylate metal salt units; and
   (b) at least one monomer containing at least two hydroxyl groups selected from the group consisting of: alkylene glycols containing 2-10 caroon atoms and their ethers; cycloalkylene glycols; Bisphenol A; hydroxy alkylene derivatives of Bisphenol A; hydroquinone; phloroglucinol; hydroxy alkylene derivatives of diphenols; glycerol; erythritol; pentaerythritol; and all natural monosaccharides.

2. The article of manufacture of claim 1 in which said means for supporting said composition is a disposable diaper.

3. The article of manufacture of claim 1 in which said means for supporting said composition is a tampon.

4. The article of manufacture of claim 1 in which said means for supporting said composition is a sanitary napkin.

5. The article of manufacture of claim 1 in which said means for supporting said composition is a surgical or dental sponge.

6. The article of manufacture of claim 1 in which said means for supporting said composition is a bandage.

7. The article of manufacture of claim 1 in which said composition is incorporated into said means for supporting in a fibrous form.

8. The article of manufacture of claim 1 in which said composition is incorporated into said means for supporting in the form of powder.

9. The article of manufacture of claim 1 in which said composition is incorporated into said means for supporting in the form of film.

10. A method of enhancing the water absorption characteristics of an article of manufacture which comprises the step of incorporating into said article a cured water absorbing composition which comprises a blend of:

(a) a copolymer containing from about 25 to about 75 mole percent recurring units of at least one $\alpha,\beta$-unsaturated monomer bearing at least one pendant unit selected from the group consisting of carboxylic acid units and derivatives of carboxylic acid units and from about 75 to about 25 mole percent recurring units of at least one copolymerizable comonomer, wherein from about 20 to about 80 percent of the total pendant units introduced through the recurring units of the $\alpha,\beta$-unsaturated monomer must either be carboxylic acid units or be converted into carboxylic acid units, and wherein from about 80 to about 20 percent of the total pendant units must either be carboxylate metal salt units or be converted into carboxylate metal salt units; and (b) at least one monomer containing at least two hydroxyl groups selected from the group consisting of: alkylene glycols containing 2–10 carbon atoms and their ethers; cycloalkylene glycols; Bisphenol A; hydroxy alkylene derivatives of Bisphenol A; hydroquinone; phloroglucinol; hydroxy alkylene derivatives of diphenols; glycerol; erythritol; pentaerythritol; and all natural monosaccharides, said composition being incorporated into said article in an effective amount to enhance at least one water-absorbing characteristic of said article as compared to the water-absorbing characteristics of the article in the absence of the composition.

11. The method of claim 10 in which said article of manufacture is a disposable diaper.

12. The method of claim 10 in which said article of manufacture is a tampon.

13. The method of claim 10 in which said article of manufacture is a sanitary napkin.

14. The method of claim 10 in which said article of manufacture is a disposable bandage.

15. The method of claim 10 in which said composition is incorporated into said means for supporting in a fibrous form.

16. The method of claim 10 in which said composition is incorporated into said means for supporting in the form of powder.

17. The method of claim 10 in which said composition is incorporated into said means for supporting in the form of film.

* * * * *